(12) United States Patent
Yamashita

(10) Patent No.: US 8,404,899 B2
(45) Date of Patent: Mar. 26, 2013

(54) ALIPHATIC AMINE ALKYLENE OXIDE ADDUCT

(75) Inventor: Seiji Yamashita, Kyoto (JP)

(73) Assignee: Sanyo Chemical Industries, Ltd., Kyoto-shi (JP)

( * ) Notice: Subject to any disclaimer, the term of this patent is extended or adjusted under 35 U.S.C. 154(b) by 286 days.

(21) Appl. No.: 12/677,591

(22) PCT Filed: Sep. 18, 2008

(86) PCT No.: PCT/JP2008/002563
§ 371 (c)(1),
(2), (4) Date: Mar. 11, 2010

(87) PCT Pub. No.: WO2009/041000
PCT Pub. Date: Apr. 2, 2009

(65) Prior Publication Data
US 2010/0204519 A1    Aug. 12, 2010

(30) Foreign Application Priority Data

Sep. 27, 2007  (JP) .................................. 2007-251744
Sep. 28, 2007  (JP) .................................. 2007-253526

(51) Int. Cl.
*C07C 213/04*     (2006.01)
(52) U.S. Cl. ........................................................ 564/475
(58) Field of Classification Search .................. 564/475
See application file for complete search history.

(56) References Cited

U.S. PATENT DOCUMENTS 3,456,012 A * 7/1969 Swenson ........................ 564/504
3,574,755 A * 4/1971 McConnell et al. ........... 564/505

FOREIGN PATENT DOCUMENTS

| JP | 56-38323 A | 4/1981 |
|----|------------|--------|
| JP | 2003-96186 A | 4/2003 |
| JP | 2005-154370 A | 6/2005 |
| JP | 2007-262249 A | 10/2007 |
| JP | 2008-013465 A | 1/2008 |

OTHER PUBLICATIONS

Database CAPLUS on STN, Acc. No. 1969:502638, Moriguchi et al., JP 44000925 B (Jan. 17, 1969) (abstract).*
Database CAPLUS on STN, Acc. No. 1957:73897, Grundland et al. Spozywczego (1957), 7, p. 34-46 (abstract).*
Database CAPLUS on STN, Acc. No. 1958:82346, Sakakibara et al., Kogyo Kagaku Zasshi (1956), 59, p. 1149-1154 (abstract).*
Database CAPLUS on STN, Acc. No. 1982:503650, Szymanowski et al., Chemia Analityczna (1981), 26(3), p. 469-475 (abstract).*
Database CAPLUS on STN, Acc. No. 1972:102747, Antropov et al., Zashchita Metallov (1972), 8(1), p. 50-55 (abstract).*
International Search Report of PCT/JP2008/002563, mailing date of Nov. 18, 2008.

* cited by examiner

*Primary Examiner* — Brian J Davis
(74) *Attorney, Agent, or Firm* — Westerman, Hattori, Daniels & Adrian, LLP

(57) ABSTRACT

An object of the present invention is to provide an aliphatic amine alkylene oxide adduct which has a satisfactory color when used as a detergent, has a sufficiently sharp molecular weight distribution, and is highly pure and less odorous. The present invention is an aliphatic amine alkylene oxide adduct formed by adding m pieces of ($A^1O$) and n pieces of ($A^2O$) [wherein $A^1O$ and $A^2O$ each independently represent an oxyethylene group and/or an oxypropylene group] to an ethylene oxide 2-mole adduct of a primary amine having a saturated or unsaturated hydrocarbon group having 4 to 24 carbon atoms, the aliphatic amine alkylene oxide adduct having a color which, as expressed by the Gardner color scale, satisfies the following expression (1) or (2):

In the case where $1 \leq m+n \leq 15$ Gardner color scale $\leq 0.5 \times (m+n+2) - 1.5$     (1)

In the case where $15 < m+n \leq 100$ Gardner color scale $\leq 6$     (2).

17 Claims, No Drawings

ALIPHATIC AMINE ALKYLENE OXIDE ADDUCT

TECHNICAL FIELD

The present invention relates to an aliphatic amine alkylene oxide adduct, and more particularly to an aliphatic amine alkylene oxide adduct in which an oxyalkylene group directly bonded to the amino group is an oxyethylene group, and which gives an unconventionally good color even when the number of total added moles of alkylene oxide is high. The present invention also relates to an aliphatic amine alkylene oxide adduct which has less impurities and a satisfactory odor even when the amount of addition of alkylene oxide is 3 moles or more, and has a narrow molecular weight distribution (Mw/Mn ratio).

BACKGROUND ART

Aliphatic amine alkylene oxide adducts, and particularly ethylene oxide adducts are used as surfactants and raw materials thereof, and the field of application covers a wide range of applications for domestic use, industrial use, agricultural use and the like, such as surfactants, auxiliary dyes for textiles, textile softening finishes, disinfectants, agrochemical spreading agents, antistatic agents and film surface modifiers.

These aliphatic amine alkylene oxide adducts are generally produced by adding an alkylene oxide to an aliphatic amine in the absence of a catalyst or in the presence of an alkali catalyst such as a hydroxide of an alkali metal or an alkaline earth metal. It has been known for long that with an amount of addition of ethylene oxide of up to 2 moles, the degree of activity of the amino group is high, and an adduct having a satisfactory color can be obtained without a catalyst.

When a reaction is carried out in the absence of a catalyst, the raw material amine is quaternized, and also, an alkyl group is detached by Hoffman degradation, producing a substance that causes coloration. Thus, although the color is satisfactory immediately after production, coloration occurs based on daily variation.

When an alkali catalyst such as a hydroxide of an alkali metal or an alkaline earth metal is used, the color is further worsened, and particularly there is a problem that coloration becomes conspicuous as the number of added moles of ethylene oxide increases.

Furthermore, conventional reactions have a problem that an aliphatic amine in the raw material or an alkoxylate as a reaction intermediate is quaternized in the presence of a trace amount of moisture or the like, and Hoffman degradation of the quaternary ammonium salt occurs under heat, thus causing generation of impurities and broadening of the distribution of added moles of alkylene oxide. Furthermore, as the degradation products have a stimulating odor, the alkylene oxide adducts have not been put into practical use for detergent applications, and particularly for domestic detergent applications.

In order to solve such problems, there have been suggested, as methods for preventing coloration, a method of performing the reaction at low temperature (for example, Patent Document 1), a method of using a metal oxide catalyst or an acid catalyst (for example, Patent Document 2), and the like.

However, even with these methods, the chance of obtaining a color improving effect is limited only to the occasions where the number of added moles of ethylene oxide is small, so that as the number of added moles of ethylene oxide increases to more than 2 moles, the color improving effect becomes insufficient. Furthermore, when the alkylene oxide adducts are used for detergent applications, a detergent power, foaming, foam breaking and odorlessness are required, but since the substances are still unsatisfactory in terms of purity, molecular weight distribution and countermeasures against foul odor, they are not put to utilization.

Patent Document 1: JP-A No. 2003-96186
Patent Document 2: JP-A No. 2005-154370

DISCLOSURE OF INVENTION

Problem to be Solved by the Invention

The present invention is intended to solve the various problems in prior art as mentioned above and to achieve the following object. That is, it is an object of the present invention to provide an aliphatic amine alkylene oxide adduct having a high number of added moles of alkylene oxide, particularly ethylene oxide, and having a satisfactory color.

It is another object of the invention to provide a highly pure and less odorous aliphatic amine alkylene oxide adduct showing a sufficiently sharp molecular weight distribution when used as a detergent, and a detergent containing this adduct as an essential component.

Means for Solving Problem

The present inventor has devotedly conducted an investigation, and as a result, the present inventor has found that when the reaction is divided into two stages, such that the reaction is carried out without a catalyst in the first stage, and degradation of the raw material amine is suppressed using a specific catalyst and the temperature conditions are strictly controlled in the second stage reaction, an aliphatic amine alkylene oxide adduct having an unconventionally satisfactory color, high purity and a sharp molecular weight distribution is obtained. Thus, the present inventor has completed the present invention.

That is, a first invention of the present application is an aliphatic amine alkylene oxide adduct represented by the following formula (1), having a color which, as expressed by the Gardner color scale, satisfies the following expression (1) or (2):

In the case where $1 \leq m+n \leq 15$, Gardner color scale $\leq 0.5 \times (m+n+2) - 1.5$     (1)

In the case where $15 < m+n \leq 100$, Gardner color scale $\leq 6$     (2)

[Chemical Formula 1]

(1)

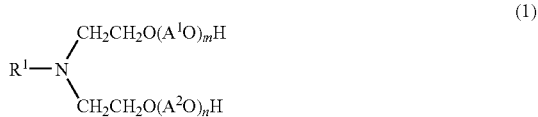

wherein $R^1$ is a saturated or unsaturated hydrocarbon group having 4 to 24 carbon atoms, or an alkoxypropyl group represented by $R^4OCH_2CH_2CH_2$; $R^4$ is a saturated hydrocarbon group having 1 to 18 carbon atoms; $A^1O$ and $A^2O$ represent an oxyethylene group and/or an oxypropylene group; and m represents the average number of added moles of ($A^1O$), and n represents the average number of added moles of ($A^2O$), and m and n are each independently a number from 0 to 50, with $m+n \geq 1$.

A second invention of the present application is an aliphatic amine alkylene oxide adduct represented by the following formula (2), having a molecular weight distribution (ratio of the weight average molecular weight Mw and the number average molecular weight Mn) which, as measured by gel permeation chromatography (GPC) using dimethylformamide (DMF) as an eluent and calculated based on a polyethylene glycol (PEG) calibration curve, satisfies the following expression (3) or (4):

$$Mw/Mn \geq 0.05 \times \ln(r+s+2)+0.975 \quad (3)$$

(provided that when $1 \leq r+s \leq 10$)

$$Mw/Mn \leq 1.10 \quad (4)$$

(provided that when $10 < r+s \leq 100$)

[Chemical Formula 2]

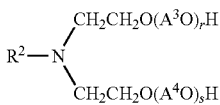

(2)

wherein $R^2$ is a saturated or unsaturated hydrocarbon group having 4 to 24 carbon atoms, or an alkoxypropyl group represented by $R^4OCH_2CH_2CH_2$; $R^4$ is a saturated hydrocarbon group having 1 to 18 carbon atoms; $A^3O$ and $A^4O$ represent an oxyethylene group and/or an oxypropylene group; r represents the average number of added moles of ($A^3O$), and s represents the average number of added moles of ($A^4O$), and r and s are each independently a number from 0 to 50, with $1 \leq r+s \leq 100$.

Effect of the Invention

The aliphatic amine alkylene oxide adduct of the present invention has less impurities or coloration, has a sharp molecular weight distribution and high purity, and is less odorous. Therefore, the substance can be suitably used in antistatic agents, textile treating agents, detergents for clothes, modifiers for paint resins, and the like. In particular, the aliphatic amine alkylene oxide adduct can be more suitably used in the fields where use thereof has been conventionally avoided owing to coloration.

BEST MODES FOR CARRYING OUT THE INVENTION

The aliphatic amine alkylene oxide adduct of the first invention and the aliphatic amine alkylene oxide adduct of the second invention of the present application are represented by the following formulas (1) and (2), respectively.

[Chemical Formula 3]

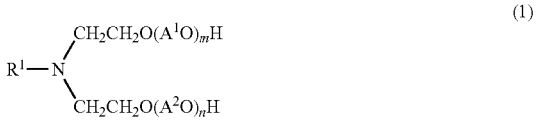

(1)

wherein $R^1$ is a saturated or unsaturated hydrocarbon group having 4 to 24 carbon atoms, or an alkoxypropyl group represented by $R^4OCH_2CH_2CH_2$; $R^4$ is a saturated hydrocarbon group having 1 to 18 carbon atoms; $A^1O$ and $A^2O$ represent an oxyethylene group and/or an oxypropylene group; and m represents the average number of added moles of ($A^1O$), and n represents the average number of added moles of ($A^2O$), and m and n are each independently a number from 0 to 50, with $1 \leq m+n \leq 100$.

[Chemical Formula 4]

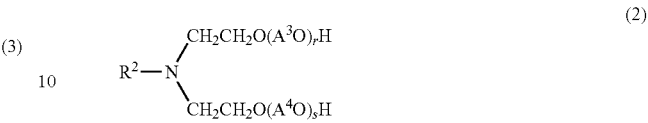

(2)

wherein $R^2$ is a saturated or unsaturated hydrocarbon group having 4 to 24 carbon atoms, or an alkoxypropyl group represented by $R^4OCH_2CH_2CH_2$; $R^4$ is a saturated hydrocarbon group having 1 to 18 carbon atoms; $A^3O$ and $A^4O$ represent an oxyethylene group and/or an oxypropylene group; r represents the average number of added moles of ($A^3O$), and s represents the average number of added moles of ($A^4O$), and r and s are each independently a number from 0 to 50, with $1 \leq r+s \leq 100$.

$R^1$ and $R^2$ in the formulas (1) and (2) each represent a saturated or unsaturated hydrocarbon group having 4 to 24 carbon atoms which may be linear or branched, or $R^4OCH_2CH_2CH_2$.

The saturated or unsaturated hydrocarbon group may be linear or branched, and usually has 4 to 24 carbon atoms. The saturated or unsaturated hydrocarbon group is preferably a linear saturated hydrocarbon group having 6 to 18 carbon atoms.

Furthermore, the alkoxypropyl group represented by $R^4OCH_2CH_2CH_2$ usually has 1 to 18, preferably 3 to 18, and more preferably 3 to 12, carbon atoms.

Specific examples of an aliphatic primary amine, which serves as a raw material, include n-butylamine, hexylamine, cyclohexylamine, octylamine, decylamine, undecylamine, dodecylamine, tridecylamine, tetradecylamine, pentadecylamine, hexadecylamine, heptadecylamine, octadecylamine, nonadecylamine, icosylamine, heneicosylamine, docosylamine, tricosylamine, tetracosylamine, octadecenylamine and octadecadienylamine; or mixtures of these, including aliphatic primary amines derived from animals and plants, such as beef tallow amine, hydrogenated beef tallow amine, coconut oil amine, palm oil amine and soybean oil amine; 3-methoxypropylamine, 3-ethoxypropylamine, 3-propoxypropylamine, 3-isopropoxypropylamine, 3-butoxypropylamine, 3-isobutoxypropylamine, 3-(2-ethylhexyl)propylamine, 3-decyloxypropylamine, 3-amine, 3-stearyloxypropylamine, and the like; and alkoxypropylamines.

The aliphatic primary amines may be used singly or as mixtures of two or more kinds. Furthermore, it is preferable that these aliphatic primary amines be purified by distillation.

Regarding the alkoxypropylamine, a product obtained by subjecting acrylonitrile to an addition reaction with an aliphatic alcohol, subjecting the nitrile group to hydrogen reduction to convert the nitrile group to a primary amine, can be used.

A third invention of the present application is a method for producing the aliphatic amine alkylene oxide adduct. The production method of the present invention includes a first stage reaction of reacting 1.5 to 2.0 moles, in terms of average number of added moles, of ethylene oxide with 1 mole of this aliphatic primary amine in the absence of a catalyst; and a second stage reaction of reacting the obtained aliphatic amine ethylene oxide adduct with 3 to 100 moles of alkylene oxide by adding 0.01 to 5% by weight of a quaternary ammonium salt as a catalyst.

The first stage reaction of producing the aliphatic amine alkylene oxide adduct of the first invention or the aliphatic amine alkylene oxide adduct of the second invention of the present application from a raw material aliphatic primary amine, is usually carried out by adding ethylene oxide in the absence of a catalyst.

The average number of added moles of ethylene oxide is 1.5 to 2.0, and preferably 1.7 to 2.0 moles.

The reaction temperature of the first stage reaction is usually 80 to 120° C., and preferably 95 to 115° C. If the reaction temperature is lower than 80° C., the induction period for the addition reaction is lengthened, and productivity is decreased.

If the reaction temperature exceeds 120° C., impurities are generated. At this time point, coloration does not occur, but the impurities affect the second stage reaction so that the aliphatic amine alkylene oxide adduct, which is the target product, is colored and odorized, and the molecular weight distribution is also broadened.

In the second stage reaction according to the present invention, a quaternary ammonium salt is used as a catalyst.

Examples of the quaternary ammonium salt include tetramethylammonium chloride, tetraethylammonium chloride, tetramethylammonium hydroxide, tetraethylammonium hydroxide, propyltrimethylammonium chloride, butyltrimethylammonium chloride, cyclohexyltrimethylammonium chloride, octyltrimethylammonium chloride, lauryltrimethylammonium chloride, a quaternization product of DBU with methyl chloride, and the like.

Among these, from the viewpoint of catalyst efficiency and environmental discharge, quaternary ammonium salts of lower alkyls (having 1 to 4 carbon atoms), which have small molecular weights and do not contain halogen, for example, tetramethylammonium hydroxide, butyltrimethylammonium hydroxide, and hydroxide of methylated DBU, can be suitably used, and furthermore, tetramethylammonium hydroxide can be more suitably used.

The amount of addition of the tetramethylammonium salt is adequately 0.01 to 5% by weight relative to the total amount upon finishing of the aliphatic primary amine alkylene oxide adduct. The amount of addition is preferably 0.02 to 1% by weight, and more preferably 0.05 to 0.5% by weight.

The alkylene oxide, $A^1O$, $A^2O$, $A^3O$ and $A^4O$, that are used in the second stage reaction according to the present invention, may be ethylene oxide or propylene oxide, and these can be used singly or as a mixture of the two kinds.

Among these, ethylene oxide can be particularly suitably used. Furthermore, when two kinds of alkylene oxide are used, the compounds may be added in a block form or may be added in a random fashion. The content ratio (molar ratio) of the oxyethylene chain and the oxypropylene chain is preferably 100/0 to 80/20, and more preferably 100/0 to 90/10. When the number of added moles of propylene oxide is increased, the rate of reaction is decreased, and productivity is deteriorated.

The number of added moles of alkylene oxide, m, n, r and s, are each independently 0 to 50 moles, and preferably 3 to 30 moles.

The numbers of m+n and r+s are each 1 to 100 moles. If the number exceeds 100 moles, the rate of reaction is decreased so that a long time is required, and thus productivity is decreased.

The reaction temperature for the second stage according to the present invention is usually 50 to 105° C., and preferably 70 to 95° C. If the reaction temperature is lower than 50° C., the reaction is slowed, and productivity is decreased.

During the reaction, if the temperature exceeds 105° C. in the presence of alkylene oxide, there occurs a side reaction between quaternary ammonium salts of the catalyst, or decomposition products (for example, a number of unspecific decomposition products such as unsaturated hydrocarbons and ketimines) of a quaternization product formed by further adding water or the like to the raw material primary amine, and alkylene oxide, so that coloration becomes conspicuous, impurities are increased, and the molecular weight distribution is also broadened.

In the addition reaction of ethylene oxide in the first stage and the addition reaction of alkylene oxide in the second stage, the pressure condition is not particularly limited, and the addition reactions can be carried out under the conventional conditions for alkylene oxide addition reactions. However, from the viewpoint of temperature control, it is preferable to carry out the addition reactions at −0.1 to 0.3 MPa.

The aliphatic amine alkylene oxide adduct of the first invention of the present application has a color which satisfies the following expression (1) or (2):

$$\text{In the case where } 1 \leq m+n \leq 15, \text{ Gardner color scale} \leq 0.5 \times (m+n+2) - 1.5 \quad (1)$$

$$\text{In the case where } 15 < m+n \leq 100, \text{ Gardner color scale} \leq 6 \quad (2)$$

The aliphatic amine alkylene oxide adduct of the present invention has a feature that the adduct not only has a satisfactory color immediately after production, but also maintains the color for a long time.

Those aliphatic amine alkylene oxide adducts produced according to general production methods are usually colored immediately after production (Comparative Examples 1 to 4 as will be described later).

When the process for heating and degradation and the process for elimination under reduced pressure concerning the catalyst are omitted after the second stage reaction in the present invention, the color immediately after the second stage may be satisfactory, but as time elapses, coloration is markedly deteriorated.

On the contrary, in the aliphatic amine alkylene oxide adduct of the present invention, coloration during storage after production and coloration under heating during actual use are hardly recognized.

According to the present invention, the Gardner color scale is determined by the method described in JIS K0071-2 (under the international standard, ISO4630-1:2004). When the Gardner color scale is 1 or lower, the Hazen unit color scale is measured. Here, in regard to the color values, a Hazen unit color scale of 300 is almost equivalent to a Gardner color scale of 1, a Hazen unit color scale of 300 or lower corresponds to a Gardner color scale of 1 or lower.

The aliphatic amine alkylene oxide adduct of the second invention of the present application has a molecular weight distribution (weight average molecular weight Mw/number average molecular weight Mn) which, as measured by gel permeation chromatography (GPC) using dimethylformamide (DMF) as an eluent and calculated based on a polyethylene glycol (PEG) calibration curve, satisfies the following expression (3) or (4):

$$\text{In the case where } 1 \leq r+s \leq 10, Mw/Mn \leq 0.05 \times \ln(r+s+2) + 0.975 \quad (3)$$

$$\text{In the case where } 10 < r+s \leq 100, Mw/Mn \leq 1.10 \quad (4)$$

The method for GPC measurement is as follows.

<Conditions for GPC Measurement>

Model: HLC-8220GPC (manufactured by Tosoh Corporation)

Column: Guardcolumn α

TSKgel α-M (all manufactured by Tosoh Corporation)

Column temperature: 40° C.

Detector: RI

Eluent: DMF containing 0.01 M LiBr

Sample concentration: 0.125%

Amount of injection: 100 μl

Sample for calibration curve: polyethylene glycol (manufactured by Tosoh Corporation; TSK STANDARD POLYETHYLENE OXIDE)

The impurities contained in the aliphatic amine alkylene oxide adduct of the present invention, which become the odorous components, can be confirmed by gas chromatography (GC).

In the impurities, there are unreacted aliphatic amine or degradation products resulting from heating, and they are detected between the solvent peak and the peak of an aliphatic amine ethylene oxide 2-mole adduct in the GC analysis. The total amount of these detected peaks is usually 0.1% or less, and preferably 0.05% or less, and it is more preferable that the peaks be undetected.

The impurity peaks cause deterioration of odor, but since the aliphatic amine alkylene oxide adduct of the present invention has fewer impurity peaks, the odor is satisfactory.

The GC measurement conditions are as follows.

<Measurement Conditions for GC>

Model: GC-1700 (manufactured by Shimadzu Corporation)

Column: Capillary Rtx-5 (30 m)

Inlet temperature: 300° C.

Detector: FID (temperature 300° C.)

Oven: initial temperature 90° C., retention time 0 minutes, rate of temperature increase 10° C./min, final temperature 300° C.

Amount of injection: 1 μl (sample is diluted 5 times with methanol)

After the addition reaction of alkylene oxide of the second stage of the present invention, a reducing agent such as sodium borohydride may be added for the purpose of preventing coloration upon catalytic degradation.

The type of the reducing agent may be, in addition to sodium borohydride, lithium borohydride, potassium borohydride, lithium aluminum hydride or the like.

The amount of addition of the reducing agent is sufficiently 10 to 1000 ppm, preferably 20 to 100 ppm, and more preferably 20 to 50 ppm, based on the aliphatic amine alkylene oxide adduct.

The temperature for addition of the reducing agent may be 70° C. or below, and a method that does not involve incorporation of air (oxygen) as far as possible is preferable. Furthermore, if the temperature is 40° C. or below, coloration does not occur if purging with an inert gas after the addition is completed within 30 minutes.

The aliphatic amine alkylene oxide adduct of the present invention preferably has an alkali metal content of 1000 ppm or less. If the alkali metal content exceeds 1000 ppm, coloration occurs based on daily variation.

EXAMPLES

Hereinafter, the present invention will be specifically described by way of Examples, but the present invention is not intended to be limited thereto.

Example 1

222 g (1.2 moles) of laurylamine (FARMIN 20D, manufactured by Kao Corporation) was introduced into a 1-L autoclave, and the autoclave was purged with argon gas and then depressurized, and the temperature was elevated to 95° C. At the same temperature, 105.6 g of ethylene oxide (2.4 moles, 2.0 moles relative to 1 mole of amine) was slowly added dropwise, while the internal pressure of the autoclave was maintained not to exceed 0.3 MPa. After an induction period of about 1.5 hours, the temperature was controlled in the range of 90 to 110° C., and the system was allowed to react for 4 hours in total. After completion of the dropwise addition, the reaction was carried out at 95° C. for 30 minutes until the internal pressure of the autoclave reached the same pressure as that at the time of initiation of dropwise addition.

3.2 g of a 25% aqueous solution of tetramethylammonium hydroxide was added to the resulting ethylene oxide 2.0-mole adduct of laurylamine while preventing air from being incorporated, and the mixture was dehydrated under reduced pressure at 95° C. for one hour. The temperature was lowered to 70° C., and then 422.4 g of ethylene oxide (9.6 moles, 8.0 moles relative to 1 mole of amine) and 69.6 g of propylene oxide (1.2 moles, 1.0 mole relative to 1 mole of amine) were added dropwise over 4 hours, while the internal pressure of the autoclave was maintained not to exceed 0.2 MPa or more, and the temperature was controlled to be at 70 to 90° C. After completion of the dropwise addition, the reaction was carried out at 70° C. for 30 minutes until the internal pressure of the autoclave reached the same pressure as that at the time of initiation of dropwise addition. Furthermore, the autoclave was subjected to pressure reduction (20 torr) at 150 to 170° C. for one hour.

The color of the resulting ethylene oxide 10-mole/propylene oxide 1-mole adduct of laurylamine (A-1) was of Gardner 1. This corresponds to m+n=9 in the expression (1), and the calculated value of the right-hand side is 4, thus the expression (1) being satisfied.

For the measured value of Mw/Mn of the resulting ethylene oxide 10-mole/propylene oxide 1-mole adduct of laurylamine (A-1), when calculation is conducted by substituting the expression (3) with 1.063 and r+s=9, the value of the right-hand side is 1.085, thus the expression (3) being satisfied. In the GC analysis, no impurity peaks were detected, and the odor was satisfactory.

Example 2

191 g (1.0 mole) of coconut (coconut oil) amine (FARMIN CS, manufactured by Kao Corporation) was introduced into a 1-L autoclave, and the autoclave was purged with argon gas and then depressurized, and the temperature was elevated to 95° C. At the same temperature, 88 g of ethylene oxide (2.0 moles, 2.0 moles relative to 1 mole of amine) was slowly added dropwise, while the internal pressure of the autoclave was maintained not to exceed 0.3 MPa. After an induction period of about 1.5 hours, the temperature was controlled in the range of 90 to 110° C., and the system was allowed to react for 4 hours in total. After completion of the dropwise addition, the reaction was carried out at 95° C. for 30 minutes until the internal pressure of the autoclave reached the same pressure as that at the time of initiation of dropwise addition.

3.2 g of a 25% aqueous solution of tetramethylammonium hydroxide was added to the resulting ethylene oxide 2.0-mole adduct of coconut amine while preventing air from being incorporated, and the mixture was dehydrated under reduced pressure at 95° C. for one hour. The temperature was lowered to 70° C., and then 220 g of ethylene oxide (5.0 moles, 5.0 moles relative to 1 mole of amine) and 58 g of propylene oxide (1.0 moles, 1.0 mole relative to 1 mole of amine) were added dropwise over 4 hours, while the internal pressure of the autoclave was maintained not to exceed 0.2 MPa or more, and the temperature was controlled to be at 70 to 90° C. After completion of the dropwise addition, the reaction was carried out at 70° C. for 30 minutes until the internal pressure of the autoclave reached the same pressure as that at the time of initiation of dropwise addition. Furthermore, the autoclave was subjected to pressure reduction (20 torr) at 150 to 170° C. for one hour.

The color of the resulting ethylene oxide 7-mole/propylene oxide 1-mole adduct of coconut amine (A-2) was of Gardner 1. This corresponds to m+n=6 in the expression (1), and the calculated value of the right-hand side is 2.5, thus the expression (1) being satisfied.

For the measured value of Mw/Mn of the resulting ethylene oxide 7-mole/propylene oxide 1-mole adduct of coconut amine (A-2), when calculation is conducted by substituting the expression (3) with 1.049 and r+s=6, the value of the right-hand side is 1.065, thus the expression (3) being satisfied. In the GC analysis, no impurity peaks were detected, and the odor was satisfactory.

Example 3

207.2 g (0.8 moles) of hardened beef tallow amine (AMINE ABT-R, manufactured by Nippon Oil & Fats Co., Ltd.) was introduced into a 1-L autoclave, and the autoclave was purged with argon gas and then depressurized, and the temperature was elevated to 95° C. At the same temperature, 70.4 g of ethylene oxide (1.6 moles, 2.0 moles relative to 1 mole of amine) was slowly added dropwise, while the internal pressure of the autoclave was maintained not to exceed 0.3 MPa. After an induction period of about 2 hours, the temperature was controlled in the range of 90 to 110° C., and the system was allowed to react for 5 hours in total. After completion of the dropwise addition, the reaction was carried out at 95° C. for 30 minutes until the internal pressure of the autoclave reached the same pressure as that at the time of initiation of dropwise addition.

4.2 g of a 25% aqueous solution of tetramethylammonium hydroxide was added to the resulting ethylene oxide 2.0-mole adduct of hardened beef tallow amine while preventing air from being incorporated, and the mixture was dehydrated under reduced pressure at 95° C. for one hour. The temperature was lowered to 70° C., and then 422.4 g of ethylene oxide (9.6 moles, 12.0 moles relative to 1 mole of amine) and 92.8 g of propylene oxide (1.6 moles, 2.0 mole relative to 1 mole of amine) were added dropwise over 6 hours, while the internal pressure of the autoclave was maintained not to exceed 0.2 MPa or more, and the temperature was controlled to be at 70 to 90° C. After completion of the dropwise addition, the reaction was carried out at 70° C. for 30 minutes until the internal pressure of the autoclave reached the same pressure as that at the time of initiation of dropwise addition. Furthermore, the autoclave was subjected to pressure reduction (20 torr) at 160 to 170° C. for one hour.

The color of the resulting ethylene oxide 14-mole/propylene oxide 2-mole adduct of hardened beef tallow amine (A-3) was of Gardner 3. This corresponds to m+n=14 in the expression (1), and the calculated value of the right-hand side is 5.5, thus the expression (1) being satisfied.

For the measured value of Mw/Mn of the resulting ethylene oxide 14-mole/propylene oxide 2-mole adduct of hardened beef tallow amine (A-3), in the case of 1.078 and r+s=14, the value of the right-hand side of the expression (3) is 1.10, and the expression (3) is satisfied. In the GC analysis, no impurity peaks were detected, and the odor was satisfactory.

Example 4

222 g (1.2 moles) of laurylamine (FARMIN 20D, manufactured by Kao Corporation) was introduced into a 1-L autoclave, and the autoclave was purged with argon gas and then depressurized, and the temperature was elevated to 95° C. At the same temperature, 105.6 g of ethylene oxide (2.4 moles, 2.0 moles relative to 1 mole of amine) was slowly added dropwise, while the internal pressure of the autoclave was maintained not to exceed 0.3 MPa. After an induction period of about 1.5 hours, the temperature was controlled in the range of 90 to 110° C., and the system was allowed to react for 4 hours in total. After completion of the dropwise addition, the reaction was carried out at 95° C. for 30 minutes until the internal pressure of the autoclave reached the same pressure as that at the time of initiation of dropwise addition.

3.2 g of a 25% aqueous solution of tetramethylammonium hydroxide was added to the resulting ethylene oxide 2.0-mole adduct of laurylamine while preventing air from being incorporated, and the mixture was dehydrated under reduced pressure at 95° C. for one hour. The temperature was lowered to 70° C., and then 422.4 g of ethylene oxide (9.6 moles, 8.0 moles relative to 1 mole of amine) was added dropwise over 4 hours, while the internal pressure of the autoclave was maintained not to exceed 0.2 MPa or more, and the temperature was controlled to be at 70 to 90° C. After completion of the dropwise addition, the reaction was carried out at 70° C. for 30 minutes until the internal pressure of the autoclave reached the same pressure as that at the time of initiation of dropwise addition. Furthermore, the autoclave was subjected to pressure reduction (20 torr) at 150 to 170° C. for one hour.

The color of the resulting ethylene oxide 10-mole adduct of laurylamine (A-4) was of Gardner 2. This corresponds to m+n=8 in the expression (1), and the calculated value of the right-hand side is 2.5, thus the expression (1) being satisfied.

For the measured value of Mw/Mn of the resulting ethylene oxide 10-mole adduct of laurylamine (A-4), when calculation is conducted by substituting the expression (3) with 1.053 and r+s=8, the value of the right-hand side is 1.063, thus the expression (3) being satisfied. In the GC analysis, no impurity peaks were detected, and the odor was satisfactory.

Example 5

229.2 g (1.2 moles) of coconut (coconut oil) amine (FARMIN CS, manufactured by Kao Corporation) was introduced into a 1-L autoclave, and the autoclave was purged with argon gas and then depressurized, and the temperature was elevated to 95° C. At the same temperature, 105.6 g of ethylene oxide (2.4 moles, 2.0 moles relative to 1 mole of amine) was slowly added dropwise, while the internal pressure of the autoclave was maintained not to exceed 0.3 MPa. After an induction period of about 1.5 hours, the temperature was controlled in the range of 90 to 110° C., and the system was allowed to react for 4 hours in total. After completion of the dropwise addition, the reaction was carried out at 95° C. for 30 minutes until the internal pressure of the autoclave reached the same pressure as that at the time of initiation of dropwise addition.

3.2 g of a 25% aqueous solution of tetramethylammonium hydroxide was added to the resulting ethylene oxide 2.0-mole adduct of coconut amine while preventing air from being incorporated, and the mixture was dehydrated under reduced pressure at 95° C. for one hour. The temperature was lowered to 70° C., and then 264 g of ethylene oxide (6.0 moles, 5.0 moles relative to 1 mole of amine) was added dropwise over 4 hours, while the internal pressure of the autoclave was maintained not to exceed 0.2 MPa or more, and the temperature was controlled to be at 70 to 90° C. After completion of the dropwise addition, the reaction was carried out at 70° C. for 30 minutes until the internal pressure of the autoclave reached the same pressure as that at the time of initiation of dropwise addition. Furthermore, the autoclave was subjected to pressure reduction (20 torr) at 150 to 170° C. for one hour.

The color of the resulting ethylene oxide 7-mole adduct of coconut amine (A-5) was of Gardner 1 or less, and thus the Hazen unit color scale was measured, which was 160. This corresponds to m+n=5 in the expression (1), and the calculated value of the right-hand side is 2.5, thus the expression (1) being satisfied.

For the measured value of Mw/Mn of the resulting ethylene oxide 7-mole adduct of coconut amine (A-5), when calculation is conducted by substituting the expression (3) with 1.039 and r+s=5, the value of the right-hand side is 1.044, thus the expression (3) being satisfied. In the GC analysis, no impurity peaks were detected, and the odor was satisfactory.

Example 6

207.2 g (0.8 moles) of hardened beef tallow amine (AMINE ABT-R, manufactured by Nippon Oil & Fats Co., Ltd.) was introduced into a 1-L autoclave, and the autoclave was purged with argon gas and then depressurized, and the temperature was elevated to 95° C. At the same temperature, 70.4 g of ethylene oxide (1.6 moles, 2.0 moles relative to 1 mole of amine) was slowly added dropwise, while the internal pressure of the autoclave was maintained not to exceed 0.3 MPa. After an induction period of about 2 hours, the temperature was controlled in the range of 90 to 110° C., and the system was allowed to react for 5 hours in total. After completion of the dropwise addition, the reaction was carried out at 95° C. for 30 minutes until the internal pressure of the autoclave reached the same pressure as that at the time of initiation of dropwise addition.

4.2 g of a 25% aqueous solution of tetramethylammonium hydroxide was added to the resulting ethylene oxide 2.0-mole adduct of hardened beef tallow amine while preventing air from being incorporated, and the mixture was dehydrated under reduced pressure at 95° C. for one hour. The temperature was lowered to 70° C., and then 563.2 g of ethylene oxide (12.8 moles, 16.0 moles relative to 1 mole of amine) was added dropwise over 6 hours, while the internal pressure of the autoclave was maintained not to exceed 0.2 MPa or more, and the temperature was controlled to be at 70 to 90° C. After completion of the dropwise addition, the reaction was carried out at 70° C. for 30 minutes until the internal pressure of the autoclave reached the same pressure as that at the time of initiation of dropwise addition. Furthermore, the autoclave was subjected to pressure reduction (20 torr) at 160 to 170° C. for one hour.

The color of the resulting ethylene oxide 18-mole adduct of hardened beef tallow amine (A-6) was of Gardner 4. This satisfies the expression (2).

For the measured value of Mw/Mn of the resulting ethylene oxide 18-mole adduct of hardened beef tallow amine (A-6), in the case of 1.069 and r+s=16, the value of the right-hand side of the expression (4) is 1.10, and the expression (4) is satisfied. In the GC analysis, no impurity peaks were detected, and the odor was satisfactory.

Comparative Example 1

259 g (1 mole) of hardened beef tallow amine (AMINE ABT-R, manufactured by Nippon Oil & Fats Co., Ltd.) was introduced into a 1-L autoclave. The autoclave was purged with argon gas, and then the temperature was elevated to 140° C. 440 g (10 moles) of ethylene oxide was injected at 140° C. over 5 hours in the absence of a catalyst. After completion of dropwise addition, the reaction was carried out at 140° C. for 30 minutes until the internal pressure of the autoclave reached the same pressure as that at the time of initiation of dropwise addition.

From the resulting hardened beef tallow amine ethylene oxide 10-mole adduct (C-1), unreacted ethylene oxide was not detected, but the color was of Gardner color scale 15. For the measured value of Mw/Mn, in the case of 1.138 and r+s=8, the right-hand side of the expression (3) is 1.08, and the expression (3) is not satisfied. Furthermore, many impurity peaks were detected in the GC analysis, and the substance had an unpleasant odor.

Comparative Example 2

259 g (1 mole) of hardened beef tallow amine (FARMIN 86T, manufactured by Kao Corporation) and 1.05 g of potassium hydroxide were introduced into a 1-L autoclave. The autoclave was purged with argon gas, and then the temperature was elevated to 95° C. 440 g (10 moles) of ethylene oxide was added dropwise at 85° C. over 10 hours. The reaction was carried out at 85° C. for 3 hours until the internal pressure of the autoclave reached the same pressure as that at the time of initiation of dropwise addition.

The color of the resulting hardened beef tallow amine ethylene oxide 10-mole adduct (C-2) was of Gardner color scale 5. For the measured value of Mw/Mn, in the case of 1.136 and r+s=8, the right-hand side of the expression (3) is 1.08, and the expression (3) is not satisfied. Furthermore, many impurity peaks were detected in the GC analysis, and the substance had an unpleasant odor.

Comparative Example 3

258 g (2.0 moles) of octylamine (FARMIN 08D, manufactured by Kao Corporation) was introduced into a 1-L autoclave, and the autoclave was purged with argon gas and then depressurized, and the temperature was elevated to 130° C. At the same temperature, 176 g of ethylene oxide (4.0 moles, 2.0 moles relative to 1 mole of amine) was slowly added dropwise. After an induction period of about one hour, the system was allowed to react at a temperature in the range of 130 to 160° C. for 3 hours in total. After completion of the dropwise addition, the reaction was carried out for 30 minutes at 130° C. until the internal pressure of the autoclave reached the same pressure as that at the time of initiation of dropwise addition.

1.0 g of N,N-dimethyldodecylamine was added to the resulting ethylene oxide 2.0-mole adduct of octylamine while preventing air from being incorporated, and the mixture was dehydrated under reduced pressure at 95° C. for one hour. 440 g of ethylene oxide (10.0 moles, 5.0 moles relative to 1 mole of amine) was added dropwise over 2 hours while the temperature was controlled to be at 110 to 130° C. After completion of the dropwise addition, the reaction was carried out at 120° C. for 30 minutes until the internal pressure of the autoclave reached the same pressure as that at the time of initiation of dropwise addition.

The color of the resulting ethylene oxide 7-mole adduct of octylamine (C-3) was of Gardner 8. For the measured value of Mw/Mn, in the case of 1.086 and r+s=5, the right-hand side of the expression (3) is 1.06, and the expression (3) is not satisfied. Furthermore, many impurity peaks were detected in the GC analysis, and the substance had an unpleasant odor.

Comparative Example 4

259 g (1.0 moles) of hardened beef tallow amine (FARMIN 86T, manufactured by Kao Corporation) was introduced into a 1-L autoclave, and the autoclave was purged with argon gas and then depressurized, and the temperature was elevated to 95° C. At the same temperature, 83.6 g (1.9 moles) of ethylene oxide was slowly added dropwise, while the internal pressure of the autoclave was maintained not to exceed 0.3 MPa. After an induction period of about 2 hours, the temperature was controlled in the range of 90 to 110° C., and the system was allowed to react for 5 hours in total. After completion of the dropwise addition, the reaction was carried out at 95° C. for 30 minutes until the internal pressure of the autoclave reached the same pressure as that at the time of initiation of dropwise addition.

4.2 g of N,N-dimethyllaurylamine was added to the resulting ethylene oxide 1.9-mole adduct of hardened beef tallow amine while preventing air from being incorporated, and the mixture was dehydrated under reduced pressure at 95° C. for one hour. The temperature was lowered to 70° C., and then 356.4 g (8.1 moles) of ethylene oxide was tried to add dropwise, but the reactivity was low. The reaction did not proceed when the internal pressure of the autoclave was less than 0.2 MPa, and the reaction was carried out by increasing the ethylene oxide concentration to exceed 0.2 MPa. However, temperature control was not possible at 105° C. or below. The maximum reachable temperature was 120° C. After completion of the dropwise addition, the reaction was carried out at 105° C. for 30 minutes until the internal pressure of the autoclave reached the same pressure as that at the time of initiation of dropwise addition. Here, the color of the resulting ethylene oxide 10-mole adduct of hardened beef tallow amine was of Hazen unit color scale 180. This was subjected to pressure reduction (20 torr) at 130 to 160° C. for one hour, and the color of the resulting ethylene oxide 10-mole adduct of hardened beef tallow amine (C-4) was of Gardner 6. For the measured value of Mw/Mn, in the case of 1.106 and r+s=8, the right-hand side of the expression (3) is 1.08, and the expression (3) is not satisfied. Furthermore, some impurity peaks were detected in the GC analysis, and a slightly unpleasant odor remained.

(A-1) to (A-6) obtained in Examples and (C-1) to (C-4) obtained in Comparative Examples were used to perform the following washing test.

<Washing Test>

Beef tallow was added with 0.1% of Sudan III (red dye) as an indicator, and 2.5 g of this was applied on a magnetic plate (diameter 25 cm). This plate was washed by rubbing at 20° C. using a sponge soaked with 3 g of each of the samples and 27 g of water (hard water containing 3.5 mg/l of calcium carbonate). Thus, the number of plates that could be washed until beef tallow was cleanly removed from the plate, was confirmed. At the same time, slipperiness in the hands, and the presence or absence of any odor remaining in the hands were confirmed. The results are shown in Table 1.

TABLE 1

| | Sample | Number of washable plates | Slipperiness in hand | Odor remaining in hand |
|---|---|---|---|---|
| Example 1 | (A-1) | 14 | Absent | Odorless |
| Example 2 | (A-2) | 14 | Absent | Odorless |
| Example 3 | (A-3) | 13 | Absent | Odorless |
| Example 4 | (A-4) | 15 | Absent | Odorless |
| Example 5 | (A-5) | 15 | Absent | Odorless |
| Example 6 | (A-6) | 14 | Absent | Odorless |
| Comparative Example 1 | (C-1) | 10 | Present | Strong |
| Comparative Example 2 | (C-2) | 11 | Present | Strong |
| Comparative Example 3 | (C-3) | 8 | Present | Strong |
| Comparative Example 4 | (C-4) | 10 | Present | Strong |

From the results described above, the aliphatic amine alkylene oxide adducts obtained in Examples 1 to 6 have colors which satisfy the expression (1) or (2), and have molecular weight distributions which satisfy any of the expressions (3) and (4). Thus, it is clear that the odor is good, and it is understood that the detergent power is higher that that of the conventional compounds. Furthermore, since the aliphatic amine alkylene oxide adducts have no odor attachment to the hands, it can be seen that the substances can be applied in the applications for domestic detergents such as kitchen detergents.

INDUSTRIAL APPLICABILITY

The aliphatic amine alkylene oxide adduct of the present invention has fewer impurities or less coloration, and is stable over a long time period. Furthermore, the aliphatic amine alkylene oxide adduct has a sharp molecular weight distribution as compared with the conventional substances. Thus, the substance of the present invention can be suitably used in antistatic agents, textile treating agents, detergents for clothes, modifiers for paint resins, and the like. Particularly, since the aliphatic amine alkylene oxide adduct of the present invention has a satisfactory odor and has a sharp molecular weight distribution as compared with the conventional substances, it can be suitably used as a detergent with high detergent power.

The invention claimed is:

1. A method for producing an aliphatic amine alkylene oxide adduct, comprising:

reacting 1 mole of an aliphatic primary amine formed by bonding a saturated or unsaturated hydrocarbon group having 4 to 24 carbon atoms or an alkoxypropyl group represented by $R^4OCH_2CH_2CH_2$ (wherein $R^4$ is a saturated hydrocarbon group having 1 to 18 carbon atoms) and hydrogen atoms, with ethylene oxide at an average number of added moles of 1.5 to 2.0 moles in the absence of a catalyst, to obtain an aliphatic amine ethylene oxide adduct (a); and further reacting the aliphatic amine ethylene oxide adduct (a) with 3 to 100 moles of alkylene oxide (b), in the presence of a quaternary ammonium salt added as a catalyst in an amount of 0.01 to 5% by weight, to obtain the aliphatic amine alkylene oxide adduct, wherein the aliphatic amine alkylene oxide adduct is represented by the following Chemical Formula (1), having a color which, as expressed by the Gardner color scale, satisfies the following expression (1) or (2):

$$\text{Gardner color scale} \leq 0.5 \times (m+n+2) - 1.5 \quad (1)$$

(provided that when $1 \leq m+n \leq 15$)

$$\text{Gardner color scale} \leq 6 \quad (2)$$

(provided that when $15 < m+n \leq 100$)

[Chemical Formula 1]

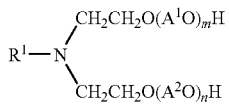
(1)

wherein $R^1$ is a saturated or unsaturated hydrocarbon group having 4 to 24 carbon atoms, or an alkoxypropyl group represented by $R^4OCH_2CH_2CH_2$; $R^4$ is a saturated hydrocarbon group having 1 to 18 carbon atoms; $A^1O$ and $A^2O$ represent an oxyethylene group and/or an oxypropylene group; and m represents the average number of added moles of ($A^1O$), and n represents the average number of added moles of ($A^2O$), and m and n are each independently a number from 0 to 50, with $1 \leq m+n \leq 100$.

2. The method for producing the aliphatic amine alkylene oxide adduct according to claim 1, wherein the quaternary ammonium salt is tetramethylammonium hydroxide, butyltrimethylammonium hydroxide or hydroxide of methylated DBU.

3. The method for producing the aliphatic amine alkylene oxide adduct according to claim 1, wherein the alkylene oxide (b) is ethylene oxide.

4. The method for producing the aliphatic amine alkylene oxide adduct according to claim 1, wherein the quaternary ammonium salt is tetramethylammonium hydroxide.

5. The method for producing the aliphatic amine alkylene oxide adduct according to claim 1, wherein $R^1$ in the formula (1) is a linear saturated hydrocarbon group having 6 to 18 carbon atoms.

6. The method for producing the aliphatic amine alkylene oxide adduct according to claim 1, wherein $R^1$ in the formula (1) is an alkoxypropyl group represented by $R^4OCH_2CH_2CH_2$ having 3 to 18 carbon atoms.

7. The method for producing the aliphatic amine alkylene oxide adduct according to claim 1, wherein in a gas chromatographic analysis, the total amount of areas of all the peaks detected between the solvent peak and the peak of the aliphatic amine ethylene oxide 2-mole adduct is 0.1% or less (solvent peak area is excluded from the calculation).

8. The method for producing the aliphatic amine alkylene oxide adduct according to claim 1, wherein the alkali metal content is 1000 ppm or less.

9. A method for producing an aliphatic amine alkylene oxide adduct, comprising:
reacting 1 mole of an aliphatic primary amine formed by bonding a saturated or unsaturated hydrocarbon group having 4 to 24 carbon atoms or an alkoxypropyl group represented by $R^4OCH_2CH_2CH_2$ (wherein $R^4$ is a saturated hydrocarbon group having 1 to 18 carbon atoms) and hydrogen atoms, with ethylene oxide at an average number of added moles of 1.5 to 2.0 moles in the absence of a catalyst, to obtain an aliphatic amine ethylene oxide adduct (a); and
further reacting the aliphatic amine ethylene oxide adduct (a) with 3 to 100 moles of alkylene oxide (b), in the presence of a quaternary ammonium salt added as a catalyst in an amount of 0.01 to 5% by weight, to obtain the aliphatic amine alkylene oxide adduct,
wherein the aliphatic amine alkylene oxide adduct is represented by the Chemical Formula (2), having a molecular weight distribution (ratio of weight average molecular weight Mw and number average molecular weight Mn) which, as measured by gel permeation chromatography (GPC) using dimethylformamide as an eluent and calculated based on a polyethylene glycol calibration curve, satisfies the following expression (3) or (4):

$$Mw/Mn \leq 0.05 \times \ln(r+s+2) + 0.975 \quad (3)$$

(provided that when $1 \leq r+s \leq 10$)

$$Mw/Mn \leq 1.10 \quad (4)$$

(provided that when $10 < r+s \leq 100$)

[Chemical Formula 2]

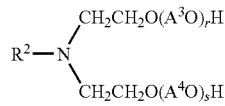
(2)

wherein $R^2$ is a saturated or unsaturated hydrocarbon group having 4 to 24 carbon atoms, or an alkoxypropyl group represented by $R^4OCH_2CH_2CH_2$; $R^4$ is a saturated hydrocarbon group having 1 to 18 carbon atoms; $A^3O$ and $A^4O$ represent an oxyethylene group and/or an oxypropylene group; r represents the average number of added moles of ($A^3O$), and s represents the average number of added moles of ($A^4O$), and r and s are each independently a number from 0 to 50, with $1 \leq r+s \leq 100$.

10. The method for producing an aliphatic amine alkylene oxide adduct according to claim 9, wherein $A^3O$ and $A^4O$ in the formula (2) are each an oxyethylene group.

11. The method for producing an aliphatic amine alkylene oxide adduct according to claim 9, wherein $R^2$ in the formula (2) is a linear saturated hydrocarbon group having 6 to 18 carbon atoms.

12. The method for producing an aliphatic amine alkylene oxide adduct according to claim 9, wherein $R^2$ in the formula (2) is an alkoxypropyl group represented by $R^4OCH_2CH_2CH_2$ having 3 to 18 carbon atoms.

13. The method for producing the aliphatic amine alkylene oxide adduct according to claim 9, wherein in a gas chromatographic analysis, the total amount of areas of all the peaks detected between the solvent peak and the peak of the aliphatic amine ethylene oxide 2-mole adduct is 0.1% or less (solvent peak area is excluded from the calculation).

14. The method for producing the aliphatic amine alkylene oxide adduct according to claim 9, wherein the alkali metal content is 1000 ppm or less.

15. The method for producing the aliphatic amine alkylene oxide adduct according to claim 9, wherein the quaternary ammonium salt is tetramethylammonium hydroxide, butyltrimethylammonium hydroxide or hydroxide of methylated DBU.

16. The method for producing the aliphatic amine alkylene oxide adduct according to claim 9, wherein the alkylene oxide (b) is ethylene oxide.

17. The method for producing the aliphatic amine alkylene oxide adduct according to claim 9, wherein the quaternary ammonium salt is tetramethylammonium hydroxide.

* * * * *